(12) United States Patent
Castan

(10) Patent No.: US 6,680,181 B2
(45) Date of Patent: Jan. 20, 2004

(54) PRODUCTION OF PEPTIDES

(75) Inventor: Andreas Castan, Hägersten (SE)

(73) Assignee: Pharmacia AB, Stockholm (SE)

( * ) Notice: Subject to any disclaimer, the term of this patent is extended or adjusted under 35 U.S.C. 154(b) by 142 days.

(21) Appl. No.: 09/732,638

(22) Filed: Dec. 8, 2000

(65) Prior Publication Data

US 2001/0005750 A1 Jun. 28, 2001

Related U.S. Application Data

(60) Provisional application No. 60/172,822, filed on Dec. 21, 1999.

(30) Foreign Application Priority Data

Dec. 9, 1999 (SE) ............................................... 9904502

(51) Int. Cl.[7] ............................ C12P 21/06; C12N 1/20; C07K 14/00
(52) U.S. Cl. .................... 435/69.1; 435/69.4; 435/71.1; 435/252.3; 530/350
(58) Field of Search ............................... 435/69.1, 270, 435/69.4, 71.1, 252.3, 252.33; 530/350

(56) References Cited

U.S. PATENT DOCUMENTS

| | | | | |
|---|---|---|---|---|
| 5,399,711 A | * | 3/1995 | Takahashi et al. | 548/453 |
| 5,763,230 A | * | 6/1998 | De Hollander et al. | 435/106 |
| 5,824,502 A | * | 10/1998 | Honjo et al. | 435/69.1 |
| 5,912,113 A | * | 6/1999 | Nakamura et al. | 435/3 |

OTHER PUBLICATIONS

Yang. "Optimization of a cultivation process for recombinant protein production by *Escherichia coli*," Journal of Biotechnology, (May 1992) 23 (3) 271–89, STN, File Medline, Abstract No. 92304528.*
Bylund et al., "Influence of Scale–Up on the Quality of Recombinant Growth Hormone," Biotechnology and Bioengineering, vol. 69, No. 2, Jul. 20, 2000.*
Gschaedler et al., Biotechnology and Bioengineering, vol. 63, No. 6, Jun. 20, 1999.*
Bhattacharya et al., Enzyme and Microbial Technology, 20: 355–360, 1997.*
Lee, Sang Yup. High cell–density culture of *Escherichia coli*. TIBTECH Mar. 1996. vol. 14, pp. 98–105.*
Dialog Information Services, Derwent Biotechnology Abstract, Dialog Accession No. 0104759, DBA Accession No. 90–07450 (1989).
Riesenberg et al, *Appl. Microbiol. Biotechnol*, 34:77–82 (1990).
Gschaedler et al, *Biotechnology and Bioengineering*, 63(6):712–720 (1999).
Bylund et al, *Bioprocess Engineering*, 20(5):377–389 (1999).
Cheng et al, *Biotechnology and Bioengineering*, 56(1):23–31 (1997).
Wang et al, *Biotechnology and Bioengineering*, 42(1):95–102 (1993).
George et al, *Bioprocess Engineering*, 18:135–142 (1998).
Lee, *Trends Biotechnol*, 14:98–105 (1996).
Bhattacharya et al, *Enzyme and Microbial Technology*, 20:355–360 (1997).
Bylund et al, *Biotechnology and Bioengineering*, 69(2):119–128 (2000).
Forsberg et al, *J. Biol Chem.* 272:12430–12438 (1997).

* cited by examiner

*Primary Examiner*—Bradley L. Sisson
(74) *Attorney, Agent, or Firm*—Dinsmore & Shohl LLP

(57) ABSTRACT

The invention relates to a method for the production of recombinant peptides by fed-batch cultivation of a microorganism in a bioreactor containing a medium comprising organic carbon source, nitrogen source and mineral salts. The cultivation is carried out by the addition of the organic carbon source by oscillation feed and/or by oscillation variation of stirring speed, e.g. in a square or sinus wave pattern. Preferably the organic carbon source is glucose and the recombinant peptide is growth hormone.

27 Claims, 3 Drawing Sheets

PRODUCTION OF PEPTIDES

This Application claims the benefit of a provisional Application No. 60/172,822 filed Dec. 21, 1999.

The invention relates to a method for the production of recombinant peptides by fed-batch cultivation of a microorganism in a bioreactor containing a medium comprising organic carbon source, nitrogen source and mineral salts. The cultivation is carried out by the addition of the organic carbon source by oscillation feed and/or by oscillation variation of stirring speed, e.g. in a square or sinus wave pattern. Preferably the organic carbon source is glucose and the recombinant peptide is growth hormone.

BACKGROUND

Recombinant human proteins have become important pharmaceuticals. The combination of recombinant DNA technology and large-scale processes has enabled production of proteins that might otherwise have been impossible or too expensive to obtain from natural sources. For instance human growth hormone (hGH), immune interferon, tissue plasminogen activator (tPA) and human insulin are now commercial available by recombinant DNA technology.

However, the organism in large-scale bioprocesses is exposed to a changing environment and also respond to this. Differences in the production of recombinant proteins have been observed when increasing the reactor size. E.g. Riesenberg D et al. in Appl Microbiol Biotechnol 34:77–82, 1990, showed that the amount of human interferon alpha 1 was reduced by a factor of two when the culture volume was increased from 15 to 250 L.

When scaling up bioprocesses, differences in the microenvironment, such as concentration, and gradients, are likely to be expected.

Concentration gradients of substrates, such as the carbon source added at limiting feed (fed-batch), ammonia for pH titration and oxygen, are to be expected as the result of changing geometry and process parameters as well as the choice of feed position. Most organisms respond to rapid environmental changes and can also change their metabolism in a time-scale of seconds or less.

Pulse addition of glucose and the oscillating glucose concentration within the fermentor have earlier been studied with regard to yield and expression.

Pulse addition of glucose, i.e. addition of glucose within a few seconds when the culture had reached the steady state, was shown to induce gapA gene expression strongly and very rapidly (Gschaedler, Anne; et al, Biotechnol. Bioeng. (1999), 63(6), 712–720).

The effect of oscillating glucose concentration within the fermentor on biomass yield and acetate formation has been studied. The conclusion was, that the lower biomass yield and the higher acetate formation were caused by the cell response to the glucose oscillation within the fermentor when comparing large and small scale cultivations. (Bylund, F et al, Bioprocess Eng. (1999), 20(5), 377–389).

Pulse addition of the growth substrate (glucose) at appropriate time intervals allowing for significant starvation period between two consecutive pulses during fed-batch cultivation have positive effects on stabilizing plasmid and enhancing protein production. (Cheng, Chinyuan et al. Biotechnol. Bioeng. (1997), 56(1), 23–31). The pulse addition was repeated for 4–5 times at about 6 hours intervals. The result shows that the periodic glucose starvation feeding strategy can maintain a stable plasmid-carrying cell fraction and a stable specific productivity of the recombinant protein. On the contrary, without glucose starvation, the fraction of plasmid-carrying cells and the specific productivity continue to drop during the fed-batch cultivation, which would greatly reduce the product yield and limit the duration that the cultivation can be effectively operated.

Wang, Zhengjun et al. Biotechnol. Bioeng. (1993), 42(1), 95–102 have shown that a glucose pulse at the end of batch culture in YPD (rich complex medium) facilitated the transport of residual cytoplasmic invertase.

U.S. Pat. No. 5,912,133 discloses a fed-batch cultivation, wherein the carbon source concentration is at a constant low level under 5 g/L and wherein the carbon source is added in at least two feedings. The carbon source should be exhausted after the first feeding and before the second feeding.

It is also known to use external magnetic field with periodic variations and product stirring movement in a cell culture vessel. (DD271850). Thereby introduced material is effectively distributed with no local and potentially damaging concentrations None of the reports disclose a repeated oscillation of organic carbon source in a square or sinus wave pattern, which can be characterized by amplitude and frequency. On the contrary it can be concluded from prior art that there should be a significant starvation period between two consecutive feedings (Cheng et al.) or that that a glucose pulse should only be done at the end of batch culture (Wang et al.).

The most applied technique to achieve high cell densities is the glucose-limited fed-batch. In a fed-batch process, all media components are supplied in excess as in a batch process, except for example the carbon source. A feed with a substrate solution, often glucose, is fed to the bioreactor with a rate that ensures that this substrate component is growth limiting. This substrate limitation allows control of the growth rate and the sugar uptake. By limiting the sugar uptake and thereby the reaction rate, engineering limitations, such as excessive heat evolution and oxygen limitation can be avoided. Glucose uptake can be divided in three reactions, glucose that is used for anabolism, glucose consumption for maintenance, which is the housekeeping requirement of the cell and glucose consumption to fuel growth. The yield in the last two reactions is approximately 1.07 $g_{O2} \, g^{-1}_{sugar}$. Control of the growth rate can therefore be used to control the oxygen consumption and heat generation associated with growth. Furthermore, substrate limitation permits metabolic control by which overflow metabolism (i.e. acetate formation in case of E. coli) and catabolite repression can be avoided. In the baker's yeast process sugar limitation is used throughout the process to avoid over-flow metabolism that results in excessive ethanol production (George et al. (1998). Bioprocess Eng 18: 135–142.). Inhibitory acetate production by E. coli is avoided in the same way (See e.g. Lee, S. Y. (1996). Trends Biotechnol 14: 98–105).

In the production of recombinant proteins the oxygen transfer and the dissolved oxygen tension is particularly important for the yield and quality of the product (See e.g. Bhattacharya and Dubey (1997) Enzyme Microb Technol 20: 355–360). A fed-batch process is therefore often the first choice when designing high-cell-density processes in E. coli.

FIGURES

THE INVENTION

Figure 1:
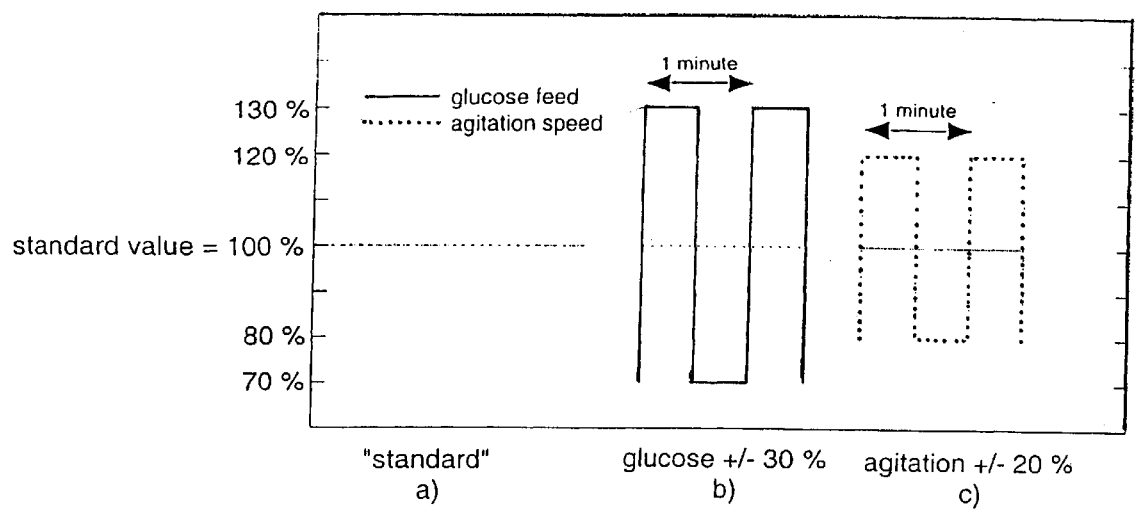
FIG. 1 shows mode of operation

We have to our great surprise found that when the glucose feed was varied in oscillation feed and/or the stirring speed was performed in oscillation variation in a fed-batch cultivation, improved rhGH quality and yield i.e. less amount of not wanted products, was obtained. The word oscillation used here can also be described as pulses or by up and down-shifts.

The invention relates to a method for the production of recombinant peptides by fed-batch cultivation of a microorganism in a bioreactor containing a medium comprising organic carbon source, nitrogen source and mineral salts. This includes also a complex cultivation media.

By the expression cultivation of a microorganism is meant cultivation of a biological host such as bacteria, yeast or animal cell.

The cultivation is carried out by the addition of the organic carbon source in oscillation feed and/or by oscillation variation of stirring speed. The oscillation feed and/or the oscillation variation of stirring speed can be performed during the entire cultivation process or during the production phase after the induction of the recombinant protein. The oscillation feed can have a square wave or sinus wave pattern. No starvation should occur during the oscillation period. The glucose added is consumed by the cells, but not until total starvation. The carbon source should never be exhausted during the process and there is no need for measuring its concentration during cultivation. The density of the cells should be high, preferably above 10 g/L and more preferably above 20 g/L and even more preferably above 50 g/L during cultivation. However, aerobic conditions should be maintained.

The biomass concentration in the experiments was in of the order of 40 g/L.

Preferably the organic carbon source is glucose and the recombinant peptide is preferably growth hormone.

The period time for the oscillation curve can easily be determined for each protein, type of cultivation, medium etc by a person skilled in the art. The period for the oscillation time can be e.g. a short time of one minute as exemplified here, but periods of five, 10, 30 minutes or longer periods are also within the scope of the invention.

The amplitude can be varied from about ±5% up to ±100%, e.g. ±20, ±30, ±40, ±50 or ±60%, which also easily is to be determined by a person skilled in the art.

Oscillation periods can be interrupted by periods of constant glucose addition or constant stirring speed.

The addition of glucose is here illustrated as a square wave function. The sinus wave function is especially suitable for the stirring speed. Also variation between sinus and square can be used.

According to our invention, the concentration of the carbon source and oxygen changes proportionally with the oscillation of the feed and agitation, respectively.

The influence of substrate feed on the quality of a recombinant protein produced by *Escherichia coli* has specifically been studied in the production of recombinant human growth hormone (rhGH) in an aerobic fed-batch process as a model system.

Our invention and the findings are further confirmed in Bylund, Castan, Mikkola, Veide and Larsson; Biotechnology and Bioengineering 69 (2), 119–128 (2000).

Materials and Methods
Organism and Medium

*Escherichia coli* (W3110) with a pBR derived plasmid coding for recombinant human growth hormone (rhGH) and antibiotic resistance was used in the performed cultivations. This rhGH form is a 22 kDa protein consisting of 191 amino acids with two intramolecular disulphide bridges. The protein is secreted to the periplasm where the disulphide bridges are formed.

Cultivations were performed in a glucose mineral salt medium. The media used, with some minor modifications, is described by Forsberg G et al. in J. Biol. Chem. 272 (1997) 12430–12438

Media components together with distilled water were sterilised in the bioreactor at 121° C. After sterilisation, sterilised magnesium sulphate, trace elements and antibiotics were added separately. Breox was added when needed for foam control. The feed solution had a glucose concentration of 590 g/l.

Cultivation Procedure and Bioreactors

Exponentially growing cells from the seed fermentor were transferred to the production bioreactor. The inoculum volume was about 10% of final total volume. After the transfer procedure the glucose feed was immediately started. The feed profile consisted of three different phases: firstly, there was an exponential feed phase; secondly, the feed was turned to constant rate when the estimated maximum oxygen transfer capacity of the bioreactor was approached and finally the feed rate was decreased to 80% of its maximum value at the time for induction.

The addition of glucose was made as a square wave function that was superimposed to the standard feed as illustrated in FIG. 1.

Temperature and pH were controlled near the optimal value for *E. coli* growth.

All cultivations were performed in a 15 l CF 3000 Chemap-Fermenter (Switzerland) stirred tank reactor (STR) with a start volume of 7 l. The volume increased during the feed phase up to 9 l.

Analytical Procedures

Samples for product analyses were achieved from the extraction of the pellet fraction of 5 ml centrifuged cell suspension. This extraction method releases the periplasmic fraction of proteins. Centrifugation was performed at 5000 rpm for 15 min at +4° C. Extraction buffer consisted of (per liter): Tris-HCl, 0.9837 g; Tris-base, 0.4551 g; EDTA× 2H$_2$O, 0.372 g. Purity and quantity of rhGH were determined by hydrophobic interaction chromatography (HIC). HIC was performed on a TSK phenyl 5PW column, Tosoh Haas. Four different variants of rhGH are separated by a decreasing salt gradient and detected with UV at 230 nm: (des-Phe1)-rhGH (LMW), rhGH, (trisulfide Cys182-Cys189)-rhGH and clipped 142/143-rhGH (clipped variant).

Results

Figure 2:
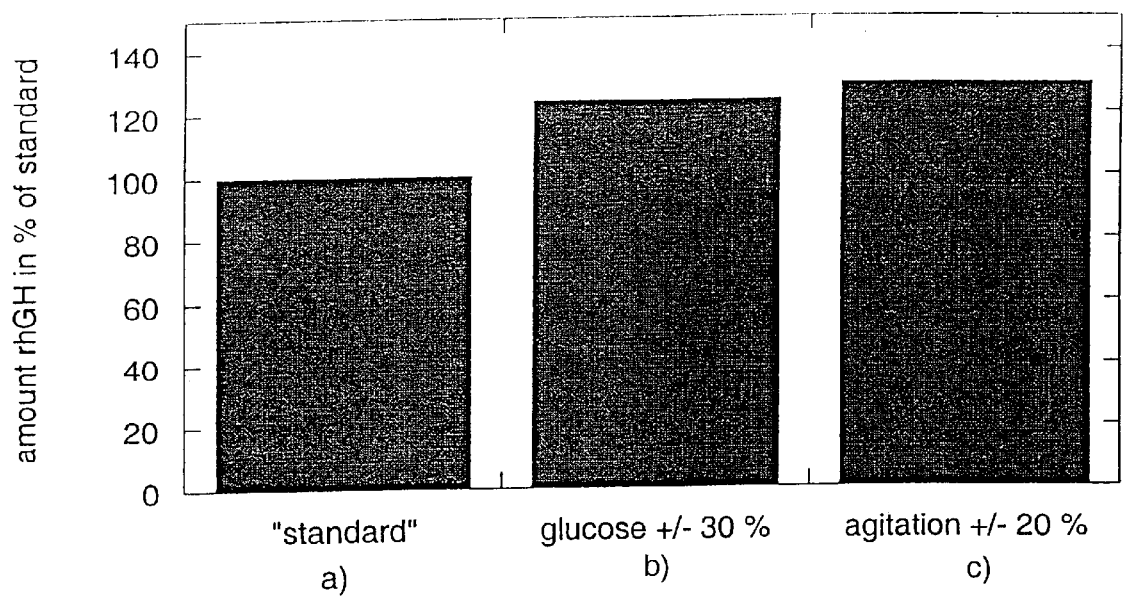
FIG. 2 shows % amount of rhGH calculated on standard.
Figure 3:
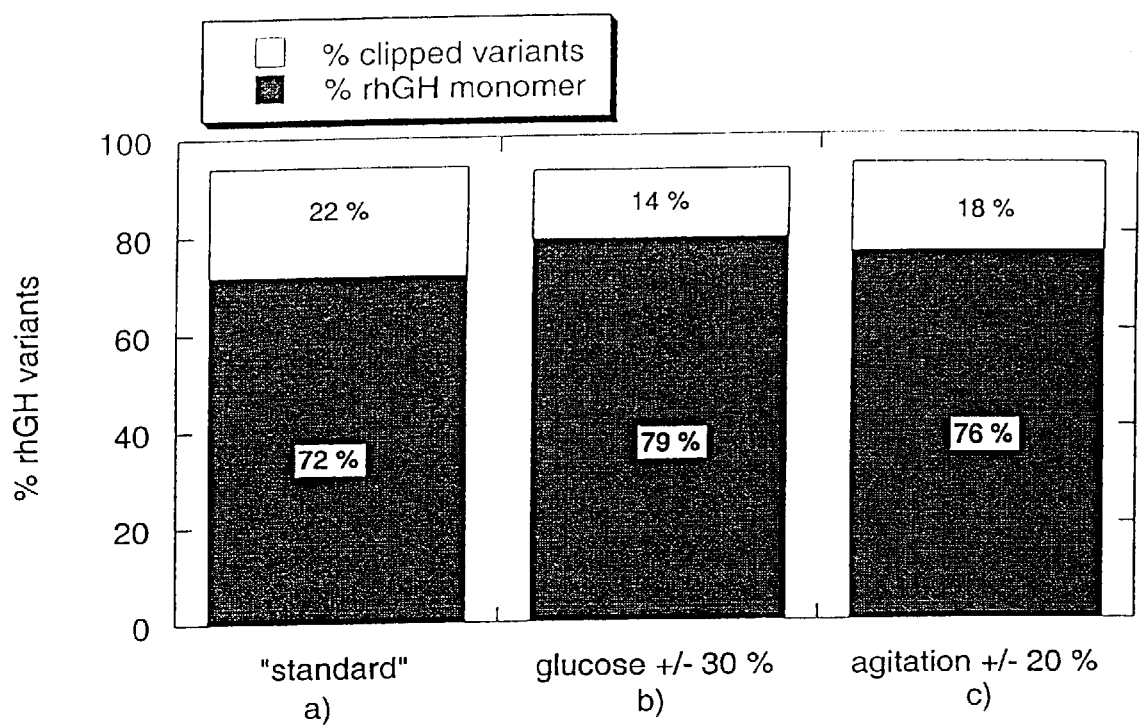
FIG. 3 shows % of rhGH variants.

The result is shown in FIGS. 2 and 3.

In the FIGS. 1–3, rhGH is produced (a) by a standard method
(b) by a glucose feed that follow a square wave with an amplitude of ±30% of the standard value and a frequency of 1 minute and
(c) by a standard glucose feed but an stirring profile (at a rate of 800–1200 rpm) that follow a square wave with an amplitude of ±20% and a frequency of 1 minute.

FIG. 2 shows the amount of rhGH when rhGH is prepared by the different methods. It is clear from the experiment that the amount of rhGH was much higher when glucose was added in an oscillation feed and by oscillation variation of stirring speed.

FIG. 3 shows the amount in % of total of rhGH 22 kDa, i.e. the proper form of rhGH (black) and the amount of clipped variants (white) when the methods (a), (b) and (c) are used. It can be seen that the yield of the proper form of rhGH, i.e. 22 kDa is higher when glucose was added in an oscillation feed and by oscillation variation of stirring speed.

Conclusions

Optimisation of the glucose feeding strategy or stirring profile by using oscillation in square or sinus wave pattern gives the advantages that the yield of the protein is higher, that proteolysis could be avoided at a higher level and that the purification thereby is easier than when the organic source is fed without oscillation feed.

What is claimed is:

1. Method for the production of recombinant peptide by fed-batch cultivation of a microorganism in a bioreactor containing a medium comprising organic carbon source, nitrogen source and mineral salts, wherein the cultivation is carried out by the addition of the organic carbon source in oscillation feed and/or by oscillation variation of stirring speed, without exhaustion of the organo carbon source during the oscillation period, wherein the oscillation has a wave period of from about 1 to about 30 minutes, wherein the microorganism is a biological host selected from the group consisting of bacteria, yeast and animal cell, and wherein the cultivation conditions remain aerobic.

2. Method according to claim 1, wherein the organic carbon is glucose.

3. Method according to claim 1, wherein the microorganism is *E. Coli*.

4. Method according to claim 1, wherein the oscillation feed has a square wave pattern.

5. Method according to claim 1, wherein the oscillation feed has a sinus pattern.

6. Method according to claim 1, wherein the recombinant peptide is growth hormone.

7. Method according to claim 1, wherein the recombinant peptide is human growth hormone.

8. Method according to claim 1, wherein the oscillation feed has a square wave function of +/−30% of standard and a wave period of 1 minutute.

9. Method according to claim 1, wherein the oscillation feed has a wave amplitude of from about +/−5% to +/−60% of standard.

10. Method according to claim 1, wherein the oscillation variation in stirring speed +/−20% of standard with a square wave period of 1 minute.

11. Method according to claim 1, wherein the microorganism is *E. coli* and wherein the recombinant peptide is human growth hormone.

12. Method according to claim 1, wherein the recombinant peptide comprises recombinant human growth hormone, immune interferon, tissue plasminogen activator, or human insulin.

13. Method according to claim 1, wherein the oscillation feed and/or oscillation variation in stirring speed is from about +/−5% to +/−60% of standard.

14. Method according to claim 2, wherein the recombinant peptide is human growth hormone.

15. Method according to claim 2, wherein the recombinant peptide is growth hormone.

16. Method according to claim 2 wherein the microorganism is *E. Coli.*

17. Method according to claim 2, wherein the oscillation feed has a square wave pattern.

18. Method according to claim 2, wherein the oscillation feed has a square wave pattern.

19. Method according to claim 3, wherein the oscillation feed has a square wave pattern.

20. Method according to claim 3, wherein the oscillation feed has a sinus wave pattern.

21. Method according to claim 3, wherein the recombinant peptide is growth hormone.

22. Method according to claim 3, wherein the recombinant peptide is human growth hormone.

23. Method according to claim 4, wherein the recombinant peptide is growth hormone.

24. Method according to claim 4, wherein the recombinant peptide is human growth hormone.

25. Method according to claim 5, wherein the recombinant peptide is growth hormone.

26. Method according to claim 5, wherein the recombinant peptide is human growth hormone.

27. Method according to claim 8, wherein the oscillation variation in stirring speed is +/−20% of standard with a square wave period of 1 minute.

* * * * *

UNITED STATES PATENT AND TRADEMARK OFFICE
CERTIFICATE OF CORRECTION

PATENT NO. : 6,680,181 B2
DATED : January 20, 2004
INVENTOR(S) : Andreas Castan

It is certified that error appears in the above-identified patent and that said Letters Patent is hereby corrected as shown below:

Column 5,
Line 21, change "organo" to -- organic --.

Column 6,
Line 2, change "stirring speed +/-20%" to -- stirring speed is +/- 20% --.
Line 23, change "square wave" to -- sinus wave --.

Signed and Sealed this

Thirtieth Day of November, 2004

JON W. DUDAS
*Director of the United States Patent and Trademark Office*